United States Patent
Hayashi et al.

(10) Patent No.: US 7,476,659 B2
(45) Date of Patent: Jan. 13, 2009

(54) LIQUID COMPOSITION FOR BULGING MUCOUS MEMBRANE FOR USE IN ENDOSCOPIC SURGERY COMPRISING A CHITOSAN DERIVATIVE CONTAINING CARBOHYDRATE CHAINS

(75) Inventors: Takuya Hayashi, Tokyo (JP); Masayuki Ishihara, Tachikawa (JP); Hirofumi Yura, Kawasaki (JP)

(73) Assignees: Netech, Inc., Kanagawa (JP); Yaizu Suisankagaku Industry Co., Ltd., Shizuoka (JP)

( * ) Notice: Subject to any disclaimer, the term of this patent is extended or adjusted under 35 U.S.C. 154(b) by 0 days.

(21) Appl. No.: 10/576,745

(22) PCT Filed: Oct. 21, 2004

(86) PCT No.: PCT/JP2004/015588

§ 371 (c)(1),
(2), (4) Date: Jul. 10, 2006

(87) PCT Pub. No.: WO2005/037292

PCT Pub. Date: Apr. 28, 2005

(65) Prior Publication Data

US 2007/0078108 A1    Apr. 5, 2007

(30) Foreign Application Priority Data

Oct. 21, 2003  (JP)  ............ 2003-360198

(51) Int. Cl.
- A61K 31/715 (2006.01)
- A61B 17/94 (2006.01)
- C07B 37/08 (2006.01)
- A61F 13/00 (2006.01)

(52) U.S. Cl. ............ 514/55; 536/20; 424/434; 606/46

(58) Field of Classification Search ............ 536/20; 514/55; 424/434; 606/46
See application file for complete search history.

(56) References Cited

U.S. PATENT DOCUMENTS 6,174,855 B1    1/2001  Hansson (Continued)

FOREIGN PATENT DOCUMENTS

JP    7-002679    1/1995

(Continued)

OTHER PUBLICATIONS

Takuya Hayashi, "Rinsyo to Kenkyu", vol. 72, No. 5, pp. 52-55, 1995.

(Continued)

Primary Examiner—Shaojia Anna Jiang
Assistant Examiner—Everett White
(74) Attorney, Agent, or Firm—Pearne & Gordon LLP

(57) ABSTRACT

The present invention provides a liquid composition to make the mucous membrane bulge during endoscopic surgery characterized in that it comprises a chitosan derivative containing carbohydrate chains. The use of the composition of the present invention as a liquid for bulging the mucous membrane during endoscopic surgery, maintain the bulge of the mucous membrane for a long period, and prevent perforation, resulting in the improved reliability of endoscopic surgery. The composition of the present invention also demonstrates prevention and inhibition of bleeding from the incised portion. The introduction of a photo-reactive group to the above chitosan derivative with carbohydrate chains allows the easy formation of a hydrogel through photo-crosslinking, leading to the further improvement in retention of the bulge and prevention of bleeding.

12 Claims, 2 Drawing Sheets

U.S. PATENT DOCUMENTS 6,624,138 B1 * 9/2003 Sung et al. .................... 514/1
6,806,260 B1 10/2004 Hirofumi et al.
7,063,715 B2 * 6/2006 Onuki et al. ................ 606/220

FOREIGN PATENT DOCUMENTS

| JP | 2000-503318 | 3/2000 |
|---|---|---|
| JP | 2003-062057 | 3/2003 |
| WO | 00/27889 | 5/2000 |

OTHER PUBLICATIONS

Tsuneo Koyama, "Endoscopic Surgery Sekkai/Hakura EMR", Nihon Medical Center, pp. 30-31, 2003.

Massimo Conio et al., "Comparative performance in the porcine esophagus of different solutions used for submucosal injection", vol. 56, pp. 513-516, issued 2002.

* cited by examiner (a) Chitosan derivative containing carbohydrate chain (b) Saline (a) Saline (b) Hyaluronate (c) Chitosan derivative containing carbohydrate chain

LIQUID COMPOSITION FOR BULGING MUCOUS MEMBRANE FOR USE IN ENDOSCOPIC SURGERY COMPRISING A CHITOSAN DERIVATIVE CONTAINING CARBOHYDRATE CHAINS

TECHNICAL FIELD

The current invention addresses a composition comprising a chitosan derivative containing carbohydrate chains. In particular, the present invention relates to a suitable composition so the mucous membranes with lesions will bulge by topically injecting it beneath the mucous membrane during EMR.

BACKGROUND ART

The application of endoscopic excision of the lesion portion of a polyp and early stage cancer (superficial cancer considered to be free from lymph-node metastasis) of alimentary tracts, including the esophagus, stomach, and colon, has been established, due to recent advances in endoscopic techniques. Although endoscopic mucosal resection (EMR) has been applied as a low-invasive surgical technique for persons whom abdominal surgery would be difficult, such as the aged and persons with serious complications, it is now the first-choice therapy for all patients in view of QOL.

EMR, in general, involves marking the lesion portion and its surrounding area, bulging the lesion portion by injecting a hypertonic saline solution into the submucosal layer of the marked region including the lesion portion, snaring and holding the portion to be removed, cutting off the tissue containing the lesion portion with the aid of a high-frequency current, and then collecting the removed tissue for histological examination (non-patent publication 1).

In order to carry out the incision of mucous membrane in EMR safely, the lesion portion must be drawn away from the muscularis propia. To do so, a liquid (referred to as "liquid for bulging the mucous membrane (or topically injectable liquid)" in this specification), such as hypertonic saline solution, is injected into submucosal layer. If the bulge (elevation) of the mucous membrane including the lesion is not sufficient, incision by snaring at a desired position becomes difficult, which may result in the failure of a reliable incision, or alternatively, perforation by incision of muscularis propia beneath the mucous membrane may be occur. Therefore, a liquid to make the mucous membrane bulge and that can retain the desired level of bulge of the mucous membrane until completion of incision is required.

Another major complication in addition to perforation, is bleeding (hemorrhage) during EMR. Accordingly, epinephrine, a vasoconstrictor, is conventionally added to the hypertonic saline solution in order to reduce bleeding volume (non-patent publication 2). However, although this reduces bleeding, some troublesome hemostatic operations cannot be avoided. In addition, when a low-viscosity liquid such as a saline solution is used as a liquid for bulging the mucous membrane, the liquid tends to leak through the needle hole or the first blade incision.

Recently, in order to overcome these problems, glucose or sodium hyaluronate have been added to the liquid for bulging the mucous membrane. It has been reported that the bulge could be prolonged to about 23 minutes on average by the addition of sodium hyaluronate in an animal experiment using porcine esophagus (non-patent publication 3). However in actuality, more than an hour, and sometimes even several hours, is required to complete EMR. Thus, a longer period to maintain the bulge is desired. On the other hand, in endoscopic submucosal dissection (ESD), a major technique used instead of the snaring method, leakage of liquid at the first blade incision is unavoidable. In addition, even if the period to maintain the bulge can be prolonged by the addition of hyalurinic acid, a hemostatic agent such as epinephrine must still also be added in order to prevent bleeding.

Non patent publication 1: Takuya Hayashi, "Rinsyo to Kenkyu", Vol. 72, No. 5, pages 52-55, 1995.

Non patent publication 2: "Endoscopic Surgery Sekkai/Hakuri EMR", Tsuneo Koyama, Nihon Medical Center, pages 30-31, 2003.

Non patent publication 3: Massimo Conio et al., Gastrointestinal Endoscopy, Vol. 56, p 513-516 (2002).

SUMMARY OF THE INVENTION

Problem to be Solved by the Invention

The problem to be solved by the present invention is to provide a liquid (a topically injectable liquid) to make the mucous membrane bulge and maintain the bulge of the mucous membrane for a longer period than currently available liquids, and improve the reliability of EMR by preventing perforation. The present invention also provides a liquid to make the mucous membrane bulge and can effectively prevent bleeding during or after surgery.

The present inventors conducted a thorough examination in order to solve the above problems, and found that the use of a liquid composition comprising a chitosan derivative containing carbohydrate chains to make the mucous membrane bulge allows an extremely long retention of the bulge of the mucous membrane, as well as preventive and inhibitory effects against bleeding.

The current invention thus provides a liquid composition (topically injectable liquid) to make the mucous membrane bulge during endoscopic surgery.

EFFECT OF THE INVENTION

According to the present invention, it is possible to maintain the bulge of the mucous membrane for a long time (24 hours or more) due to the viscous property of the chitosan derivative containing carbohydrate chains. Furthermore, it is also possible to reduce the volume of bleeding, because the chitosan derivative surrounds and encloses the hemorrhagic focus. As a result, the present invention can solve the two major problems in EMR therapy, perforation and bleeding.

In consideration of the above advantages, the composition of the present invention can be applied to areas of gastrointestinal tract other than the gastric mucosa during remote-controlled surgery using an endoscope or laparoscope, such as colon polypectomy (endoscopic excision of colon polyp), laparoscopic gastrectomy, treatment of esophagus aneurism, etc. Therefore, the term endoscopic surgery is not restricted to excision of gastric mucosa, but includes all remote-controlled surgeries using an endoscope or laparoscope.

EXPLANATION OF THE SYMBOLS

Figure 1:
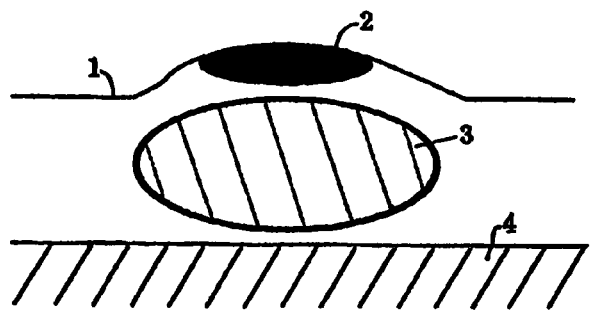
FIG. 1 is a schematic diagram showing cross-sectional view of tissue surrounding the mucous membrane in which a liquid for bulging the membrane was topically injected.

1: mucous membrane, 2: lesion, 3: liquid for bulging mucous membrane, 4: muscularis propia.

BEST MODE FOR CARRYUNG OUT THE INVENTION

The chitosan derivative containing carbohydrate chains to be admixed to the liquid composition for bulging mucous membrane of the present invention is preferably a chitosan derivative whose water-solubility has been improved by incorporating a carbohydrate chains such as lactose into the chitosan backbone. For example, as the chitosan derivative usable in the present invention, those described in WO 00/27889 can be listed. More specifically, the chitosan derivative preferably has a structure in which a carbohydrate chain and optionally a photo-crosslinkable group are introduced into a polymer backbone, which is generally called as chitin/chitosan. In particular, those formed by incorporating a carbohydrate having reducing terminals and a photo-reactive functional group to at least a part of the 2-position amino groups in the glucosamin units constituting an at least partially deacetylated chitin/chitosan are preferable.

The chitosan derivatives suitable for the present invention are those formed by incorporating a carbohydrate having reducing terminals to at least a portion of the 2-position amino groups in the glucosamin units (1) constituting the above-described chitosan and a photo-reactive functional group to at least another portion of the 2-position amino groups. Details of such chitosan derivatives are described in WO0/27889.

Normally, chitin/chitosans are deacetylated acid-soluble fractions obtained by alkali processing chitin (poly-N-acetylglucosamins) originated from crab shells, and generally have the constituent units expressed by the following formulas (1) and (2).

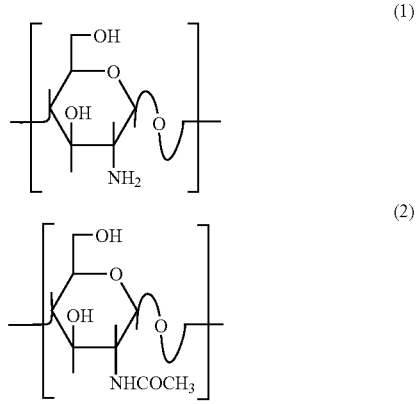

Among chitin/chitosans, some persons call those having a low degree of deacetylation (normally less than 40%) as "chitins" and those having a high degree of deacetylation (normally 40% or more) as "chitosans", but henceforth in the present specification, all chitin/chitosans which are at least partially deacetylated shall be referred to collectively as "chitosans". Additionally, in the present invention, chitosans are not limited to those of natural origin, and may be chemically modified carbohydrate chains having similar structures synthesized chemically or by genetic engineering.

Here, "degree of deacetylation" refers to the proportion of acetylamino groups in the 2-position of the carbohydrate units constituting the chitosan (or poly-N-acetylglucosamin), which have been converted to free amino groups by deacetylation. In the present specification, the degree of deacetylation is measured by means of the "colloidal titration method" described in "Health Foods Standard and Criterion (No. 4)", Japan Health Food and Nutrition Food Association (1996), p. 55.

The chitosan derivative of the present invention has been functionalized by further chemically modifying the chitosan, and the chitosan used as the raw material should preferably have a degree of deacetylation of at least 40%, preferably 60-100%, more preferably 65-95%. A chitosan having a 100% degree of acetylation consists entirely of the constituent units of the above-given formula (1), and does not include the constituent units of formula (2).

Additionally, there are no particular restrictions on the molecular weight of the chitosan, and this can be changed of a wide range depending on the projected use of the chitosan derivative, but in general, the number-average molecular weight should be in the range of 5,000-2,000,000, preferably 10,000-1,800,000, more preferably 40,000-1,500,000.

The carbohydrates having reducing terminals to be incorporated to the chitosan derivatives include aldoses and ketoses, among which those having 20 or less constituent carbohydrate units, especially those with 1-7 units are preferably used. Specific examples include pentaoses and hexaoses such as glucose, fructose, galactose, fucose, mannose, arabinose, xylose, erythrose, hepturose and hexylose, amino carbohydrates such as glucosamin, N-acetylglucosamin and galacsamin; carbohydrate derivatives such as uronic acids and deoxysaccharides; di- and trisaccharides such as maltose, isomaltose, lactose, melibiose and maltotriose composed of carbohydrate chains combining the above-mentioned monosaccharides; and the various oligosaccharides, among which the neutral disaccharides such as maltose, lactose and melibiose are preferable.

While it is also possible to derive chitosans from organic compounds such as polyethers and polyhydric alcohols instead of the above-mentioned carbohydrates, it is preferable to use natural carbohydrate chains in consideration of biocompatibility.

The incorporation of the above-mentioned carbohydrates in the 2-position amino group of the glucosamin units of the chitosan of the above-given formula (1) can itself be performed using known methods. For example, methods of carboxylating the reducing terminal of a carbohydrate, then binding to the 2-position amino group by an amide bond (see, for example, Japanese Patent Application, First Publication No. H10-120705), or of aldehydating or carbonylating the reducing terminal of a carbohydrate, then binding to the 2-position amino group of a glucosamin unit by a reduction alkylation method by means of a Schiff base (see, for example, "Applications of Chitins and Chitosans", edited by Chitin/Chitosan Workshop, pp. 53-56, Feb. 20, 1990, published by Gihodo Shuppan KK).

The carbohydrate incorporated in the chitosan in the present invention is not limited to only one type, and it is possible to use a combination of 2 or more.

Specific examples of a carbohydrate side chain constituting the chitosan derivative of the present invention include the following, but there is no restriction to these.

(i) Carbohydrate derived from lactose:

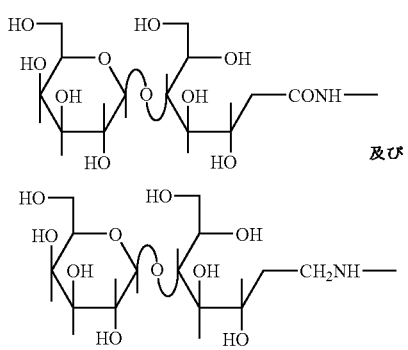

(ii) Carbohydrate derived from maltose:

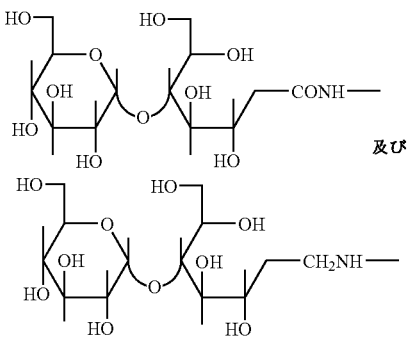

(iii) Carbohydrate derived from melibiose:

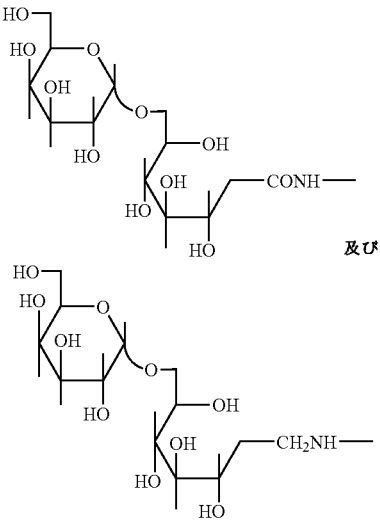

(iv) Carbohydrate derived from cellobiose:

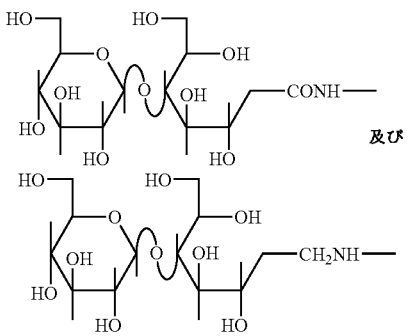

(v) Carbohydrate derived from laminalibiose:

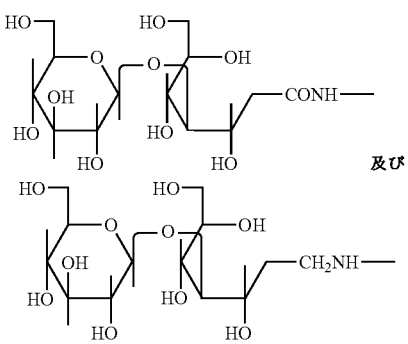

(vi) Carbohydrate derived from mannobiose:

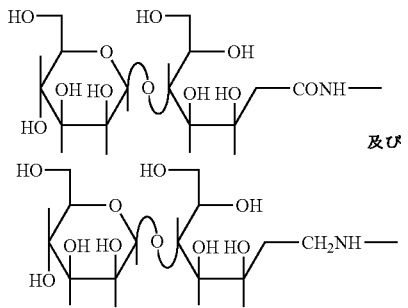

(vii) Carbohydrate derived from N-acetylchitobiose:

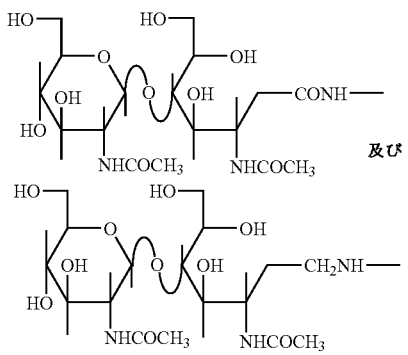

Of the carbohydrate side chains given in the above (i)-(vii), those on the left side represent residual groups incorporated by means of condensation between a carboxyl group on the carbohydrate and a 2-position amino group on the chitosan, while those on the right side represent residual groups bound by a Schiff base.

The acid-depending solubility of the chitosan is relieved by introducing the carbohydrate chains to the 2-position of the glucosamine unit of chitosan, and solubilization at neutral region can be accomplished.

While the degree of substitution of 2-position amino groups in the glucosamin units of chitosan by carbohydrate side chains can be changed depending on the physical properties desired in the final chitosan derivative, the degree of substitution should generally be in the range of 0.1-80%, preferably 0.5-60%, more preferably 1-40%. Here, the "degree of substitution" of the carbohydrate side chain is the level to which the amino groups in the 2-position of the carbohydrate units constituting the chitosans are substituted by carbohydrate side chains, and denote the proportion of substituted amino groups with respect to the total number of free amino groups and substituted amino groups at the 2-position of the carbohydrate units constituting the chitosans. In the present specification, the degree of substitution of carbohydrate side chains is measured by the "phenol-sulfuric acid method" wherein the characteristic color emission due to a reaction between carbohydrate chains and phenol in sulfuric acid is sensed by light absorption at 490 nm (see J. E. Hodge, B. T. Hofreiter, "Methods in Carbohydrate Chemistry", ed. by R. L. Whistler, M. L. Wolfrom, vol. 1, p. 388, Academic Press, New York (1962)).

The chitosan derivative of the present invention preferably has a self-crosslinking property by photo-irradiation due to incorporating photo-reactive functional groups in the 2-position amino groups in the glucosamin units of the above-given formula (1) constituting the chitosan. By using the chitosan derivative having photo-reactive functional groups, the composition can form an insoluble hydrogel by irradiation with light such as UV after infusing the composition below the mucous membrane, which results in further improvement of shape-keeping ability (ability for maintaining bulge of mucous membrane).

The photo-reactive functional groups used for chemical modification of the chitosans according to the present invention are groups which react with each other and/or amino groups or hydroxyl groups present in the chitosan upon irradiation by ultraviolet light including the near-ultraviolet region of 200-380 nm to form crosslinking bonds including, for example, those derivable from cyclic unsaturated compounds such as benzophenones, cinnamic acids, azides, diolefins and bis-anthracene, especially preferable being those having carbonylazide groups, sulfonylazide groups and aromatic azide groups.

Specific examples of a photo-reactive group to be incorporated into the chitosan derivative of the present invention include, for example, those expressed by the following formulas (A) through (E), which are UV-reactive groups. The group of formula (A) is derived from p-azidobenzoic acid, the group of formula (B) is derived from p-azidobenzaldehyde, the group of formula (C) is derived from p-benzoylbenzoic acid, the group of formula (D) is derived from cinnamic acid, and the group of formula (E) is derived from 1-methyl-4-[2-formylphenyl]ethenyl]pyridinium.

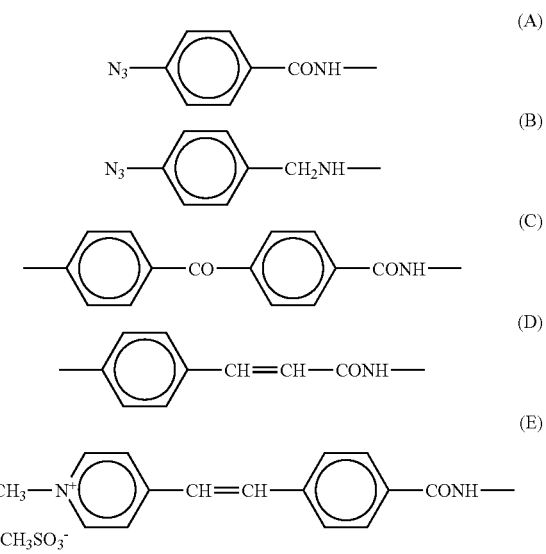

The photo-reactive group may be a substitutional group which reacts by irradiation of visible light of about 400 to 500 nm. Such visible-light-reactive groups include, for example, formyl styryl group represented by the following formula and described in Journal of Polymer Science: Polymer Chemistry Edition, Vol. 20, 1419-1432 (1982).

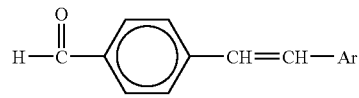

(In this formula, Ar denotes a heterocyclic ring such as pyridine, alkylpyridinium salt, quinolin, or alkylquinolinium salt.)

The incorporation of photo-reactive functional groups can itself be performed by known methods, for example, by a method of binding an azide compound having a carboxyl group to the 2-position amino group in the presence of a condensing agent (see Japanese Patent Application, First Publication No. H 10-120705); or a method of reacting the azide compound with the 2-position amino group by means of an acid chloride group, an aldehyde group, an N-hydroxysuccinic acid imide ester group or an epoxy group (see "Applications of Chitins and Chitosans", edited by Chitin/Chitosan Workshop, pp. 53-5645-65, Feb. 20, 1990, published by Gihodo Shuppan KK). The above-described formyl styryl compound can be incorporated by coupling its formyl group with the amino group of chiotosan.

While the degree of substitution of these photo-reactive functional groups can be changed according to the degree of gelification (insolubility) due to the crosslinking reaction desired in the final chitosan derivative, but it is preferable for the degree of substitution of the photo-reactive functional groups to be within the range of 0.1-80%, preferably 0.5-50%, more preferably 1-30%. Here, the "degree of substitution" of the photo-reactive functional groups is the degree of substitution of the 2-position amino groups of the carbohydrate units forming the chitosans with photo-reactive functional groups, and is the proportion of substituted amino groups with respect to the total number of free amino groups and substituted amino groups at the 2-position of the carbohydrate units forming the chitosans. In the present specification, the degree of substitution of photo-reactive functional groups such as azide groups can be determined based on calibration curves obtained from characteristic absorption at 270 nm for 4-azidobenzoic acid.

The degree of substitution of the total of carbohydrate side chains and photo-reactive functional groups in the chitosan derivatives of the present invention is not particularly restricted, and may vary over a considerable range, but is usually in the range of 0.2-80%, preferably 1.5-65%, more preferably 3-50%.

Additionally, according to the present invention, a hydrogel with considerably improved water retention ability can be obtained by incorporating an amphipathic group to at least a portion of the 3- or 6-position hydroxyl groups in the carbohydrate units of formulas (1) and (2), and the amino groups in the 2-position of the carbohydrate units of formula (1) constituting the chitosan. These amphipathic groups are groups having a hydrophobic block comprising a hydrophobic group and a hydrophilic block comprising a hydrophilic group, and often have a surfactant function. Among these those in which the molecular weight ratio between the hydrophobic blocks (X) and the hydrophilic blocks (Y) is X:Y=1:5 to 5:1 are preferably used, and non-ionic groups without dissociated ionic groups are more preferably used. In particular, those composed of a hydrophobic alkyl block and a hydrophilic polyoxyalkylene block and with a molecular weight of at least 90 are preferable, a polyoxyalkylene alkyl ether of 500-10,000 being more preferable. While a polyether not having a hydrophobic block may be used, a polyoxyalkylene alkyl ether is preferable for having both a hydrophobic block and a hydrophilic block in consideration of the improvement to the water retaining ability.

The incorporation of these amphipathic groups to the chitosan can be performed, for example, by a method of incorporating a compound having groups capable of reacting with amino groups to form covalent bonds, such as aldehyde groups or epoxy groups to a terminal portion of either the hydrophilic block or hydrophobic block of the amphipathic group, then reacting with the 2-position amino group of the glucosamin of the chitosan, a method of inducing a reaction between a polyoxyalkylene alkyl ether derivative having a carboxyl group with the chitosan in the presence of a condensing agent, or a method of inducing a reaction between a polyoxyalkylene alkyl ether derivative having an acid chloride group with a hydroxyl group or amino group in the chitosan.

For example, when incorporating a polyoxyalkylene alkyl ether group with an epoxy group on its terminal into an amino group in the chitosan, the amphipathic group is expressed by the following formula (a), and when incorporating a polyoxyalkylene alkyl ether group with an aldehyde group on its terminal into an amino group of the chitosan, the amphipathic group is expressed by the following formula (b). Additionally, when binding a polyoxyalkylene alkyl ether group with an acid chloride group on its terminal to the 3- or 6-position hydroxyl group of the chitosan, the amphipathic groups are expressed by the following formula (c). In the below formulas (a)(c), n and m are repeating units numbering 1 or more.

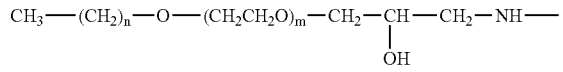
(a)

-continued
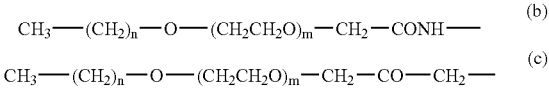

The degree of incorporation of amphipathic groups in the chitosan derivatives of the present invention is not particularly restricted, but should be within the range normally of 5-70%, preferably 15-55% based on the change in weight of the chitosan derivative after incorporation.

The liquid composition for bulging mucous membrane can be prepared as a liquid formulation by dissolving the above-described chitosan derivative containing carbohydrate chains in a physiologically acceptable medium such as water or water-alcohol mixed solvent.

The liquid for bulging mucous membrane is topically injected with, in general, a needle of about 23 G (gauge). Accordingly, the liquid must be injectable through the needle. In addition, the liquid for bulging mucous membrane preferably has a viscosity sufficient to stand it against flux of blood. Furthermore, the liquid for bulging mucous membrane preferably stay in submucosal layer after the mucous membrane is removed by EMR or ESD. In consideration of these conditions, the composition of the present invention contains 0.5-8.0, preferably 1.0-5.0, more preferably 2.0-3.0, most preferably about 2.5% by weight of the chitosan derivative containing carbohydrate chains (molecular weight of about 1,000,000). The liquid for bulging mucous membrane thus prepared has a low viscosity of about 300 cps (centipoises (mPa·s)) or less, about 200 cps or less, or about 100 cps or less measured with a commercially available rotary viscometer (for example, B type viscometer, manufactured by TOKIMEC Inc. (Tokyo, Japan)).

The chitosan derivative preferably used in the present invention becomes well soluble in neutral regions by introducing the carbohydrate chains, can be made into a solution by a physiological buffer or a culture media, and can be mixed without losing the activity of drugs, such as proteins, that may get denatured by acid or alkali.

For example, the composition of the present invention itself has a sufficient hemostatic property, however, the ability to prevent bleeding may be improved by admixing other agents having a hemostatic property such as epinephrine, or the wound healing effect (or recurrent preventing effect) may be added by admixing antitumor agents.

Further, by introducing the photoreactive group, an insoluble gel body may be formed immediately by light irradiation after application to an appropriate region, which adheres to tissues, and a wound healing promoter may be enclosed therein and sustained-released later.

In addition, when the chitosan derivative having photo-reactive groups is used, it forms an insoluble gel immediately with light-irradiation after injecting the liquid composition into submucosal layer, whereby the bulge of mucous membrane maintains for unexpectedly long term. Furthermore, the hydrogel formed by photo-crosslinking may act as a matrix, which can sustained-release the agents incorporated therein.

Conditions for crosslinking by light vary according to the types and degree of substitution of the photoreactive groups introduced into the photo-crosslinkable chitosan derivative to be used, amounts of the chitosan derivative contained in the composition and amounts of the composition to be injected and desirable hardness and the like. In general, when about 30 µl of a composition containing about 2.5 mg/ml of the photo-crosslinkable chitosan derivative is used, light irradiation from a light source provided at about 2 cm from the composition is conducted for about 0.01 to 100 sec, preferably about 0.02 to 60 sec, more preferably about 0.1 to 30 sec, and most preferably several seconds and thereby suitable gel having a desirable hardness can be obtained. The crosslinking reaction degree of the photoreactive group of the chitosan matrix is not particularly limited. In general, it is considered that there is a trend that when the crosslinking reaction degree is high, the hydrogel formed becomes hard.

The photo-irradiation may be conducted after injection of the liquid composition for bulging and before incision of lesions, or alternatively, it may be conducted to the exposed composition after incision of lesions. In the former case, the composition may be gelled by light irradiated through an optical fiber integrated with a needle for injection of the composition. In the latter case, light may be irradiated to the exposed composition through an optical fiber inserted through a channel for an endoscopic instrument.

The concept has not been proposed in which a property (for example, photo-crosslinkable property) for making it insoluble (solid) due to a physicochemical trigger is rendered to a liquid for bulging mucous membrane to be injected, whereby improving holding ability thereof by making insoluble (solid) after injection. The inventors firstly accomplished such a new approach.

We found that the composition of the present invention has an effect for the prevention of bleeding when the composition was not irradiated with light. We believe this is due to the viscosity of the composition and the property of chitosan. The hydrogel formed by light-irradiation exhibited remarkably superior hemostatic effect. For example, hemostasis was obtained within 10 minutes or less, under the condition in which a normal hemostasis was difficult due to heparinization. This means that the composition of the present invention has sufficient effects to control and prevent bleeding in EMR even when no hemostatic agent is used.

Further, when an amphipathic group such as polyoxyalkylene alkylether is introduced into the photo-crosslinkable chitosan derivative, the crosslinked chitosan hydrogel becomes able to rapidly absorb lots of moisture close to 100 times its own weight. Accordingly, the crosslinked chitosan hydrogel can absorb bleeding from the wound region to accelerate hemostasis and healing.

The composition of the present invention is preferably provided as a liquid sterilized with autoclave. The autoclave sterilization is also called as high-pressure steam sterilization, and is a method for sterilization by heating with saturated water vapor having a predetermined temperature and pressure. For example, in the Japanese Pharmacopoeia, sterilization conditions of 30 minutes at 115° C., 20 minutes at 121° C, and 15 minutes at 126° C. are described.

When the composition of the present invention is sterilized in the form of liquid filled in a container, its properties are not degraded but its viscosity decreases, thereby usability of the composition is improved. For example, if the composition containing a chitosan derivative having photo-reactive groups is used, the photo-reactive groups do not denature by the autoclave sterilization, and the composition suitably forms a hydrogel by light-irradiation. Accordingly, the liquid composition for bulging mucous membrane of the present invention can be provided as a ready-to-use sterilized liquid form.

The present invention will next be described in detail using concrete examples. However, these concrete examples do not limit the scope of the present invention.

EXAMPLES

Example 1

Synthesis of Photo-Crosslinkable Chitosan Derivative

A photo-crosslinkable chitosan derivative containing carbohydrate chains (referred to as "Az-CH-LA") was synthesized according to the method described in WO00/27889. More specifically, chitosan with a molecular weight of 300 to 600 kDa and 80% deacetylation degree (available from Yaizu Suisan Industry Co., Ltd.) was used as the raw material. Azide (p-azide benzoate) and lactose (lactobionic acid) were introduced through condensation reaction with the amino groups of the above-described chitosan. Substitution degrees of p-azide benzoate and lactobionic acid were 2.5% and 2.0% of the amino groups, respectively. It was confirmed that the resultant was soluble in neutral pH due to the introduction of lactose.

An aqueous solution of Az-CH-LA (20-30 mg/ml) was prepared. It was converted into an insoluble hydrogel by UV irradiation at a lamp distance of 2 cm [UV-irradiation system: Spot Cure ML-251 C/A with a guide fiber unit (SF-101BQ) and a 250 W lamp (240-380 nm); Ushio Electrics Co. Ltd., Tokyo Japan] through crosslinking reaction.

Example 2

Measurement of the Thickness of the Submucosal Layer

Sprague-Dawley rats (15-16 weeks, all male with average body weight 325±15 g; SLC Japan) were used in this example. After overnight fasting, the rats were anesthetized with pentobarbital (25 mg/kg), and the mucous membrane of the glandular stomach was exposed by sterile anterior gastrostomy after laparatomy. A 2.5% Az-CH-LA aqueous solution (0.3 ml) or saline solution (0.3 ml) was injected into the submucosal layer of the posterior wall through a 25 G stainless-steel needle. After injection, the mucosal surface was observed for 30 minutes, and 5 rats from each group were euthanized by an overdose of anesthesia. In the remaining rats, 10 ml of saline solution was injected into the subcutaneous space 30 minutes after treatment to prevent dehydration, and the stomachs and abdomens were closed. These rats were euthanized 6 hours (n=5 for each group) or 24 hours (n=5 for each group) later. Tissue was removed and fixed in 10% formalin for 2 days. Afterwards, the thickness of the submucosal layer was measured by microscopic observation of the cross-sectional views of the fixed specimens. The specimens were also embedded in paraffin, sectioned, and stained with hematoxylin-eosin (HE) reagent.

Figure 2:
FIG. 2 are microscopic photographs showing the cross-sectional view of tissue surrounding the mucous membrane 30 minutes after injection into the submucosal layer of (a) an aqueous solution of chitosan derivative containing carbohydrate chains, and (b) saline solution.

After injection of Az-CH-LA solution or saline, the mucosal surfaces were elevated similarly. In the Az-CH-LA-injected group, the elevated area showed a bulge 30 minutes after injection as steep as that just after injection, but in the saline-injected group, the bulge had become noticeably less steep within 30 minutes (FIG. 2). The thickness of the submucosal layer at various time-points is shown in Table 1. The results in Table 1 are expressed as mean +/−S.E., and were analyzed using Mann-Whitney U-test with the significance level set at P<0.05.

TABLE 1

|  | 30 minutes | 6 hours | 24 hours |
| --- | --- | --- | --- |
| Az-CH-LA-injected group | 3.8 ± 0.1 | 4.0 ± 0.1 | 4.1 ± 0.1 |
| Saline-injected group | 2.0 ± 0.2 | 1.9 ± 0.3 | 1.8 ± 0.3 |

Values (mm) are mean ± S.E. (n = 5 for each group)

At any time-point within the 24 hours, the submucosal layers of the rats of the Az-CH-La-injected group were significantly thicker than those of the saline-injected group. It is suggested that in the saline-injected group, all of saline leaked out within 30 minutes, since thickness did not change after 30 minutes. Histological examination revealed that Az-CH-LA, which exhibits homogeneous eosinophilic staining, was retained in the submucosal tissue.

Example 3

Measurement of the Volume of Bleeding

Heparin (300 units) was injected intravenously prior to injection of 2.5% Az-CH-LA aqueous solution or saline solution using the same method as described in Example 2. The mucous membrane (5-6 mm in diameter) around the top of the bulged (elevated) area of the mucous membrane was incised using a surgical blade. In Az-CH-La group, the incised wound was immediately irradiated with UV light for 30 seconds using the UV-irradiation system described above. Blood issuing from the stomach in each rat was collected with a surgical swab, and the volume of bleeding was estimated by the increase in weight of the swab (n=10 for each group). Measurement was performed 4 times in every 5 minutes, and the animals were then euthanized with an overdose of anesthesia. Stomachs were resected for histological examination. The removed tissues were fixed in 10% formalin for 2 days, embedded in paraffin, sectioned, and stained with hematoxylin-eosin (HE) reagent.

In the Az-CH-LA-injected group, blood issued from the incised mucosal edge or gap between the mucosal edge and Az-CH-LA (prior to irradiation). Bleeding almost completely stopped within 5-10 minutes after UV-irradiation, demonstrating that the generated gel effectively acted as a glue to seal the opening. In the saline-injected group, bleeding continued for over 20 minutes after incision.

Figure 3:
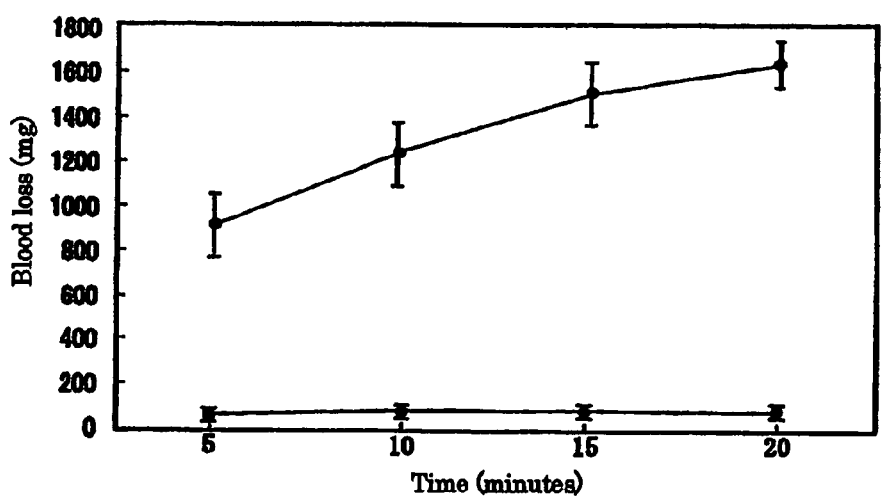
FIG. 3 is a graph showing the time-dependent change of cumulative amount of bleeding (blood loss) after injection of (a) chitosan derivative containing carbohydrate chains and (b) saline solution into the submucosal layer, followed by incision of the mucous membrane.

Blood loss in the first 5-minutes after mucosal incision was 63.1±14.2 mg in the Az-CH-LA injected group, and 922.9±143.6 mg in saline-injected group (P<0.01) (FIG. 3). The cumulative volumes in the Az-CH-LA-injected group were 93.2±10.5 mg at 10 minutes, 106.4±15.2 mg at 15 minutes, and 113.0±15.5 mg at 20 minutes. In contrast, the corresponding values of the saline-injected group were 1268.0±105.5 mg, 1537.2±125.4 mg, and 1682.3±95.2 mg, respectively. These values (blood loss) were plotted against time in FIG. 3. The blood loss in Az-CH-LA-injected group was significantly smaller than that of saline-injected group. Histological observation of the specimens showed that the bleeding focus was completely surrounded by chitosan hydrogel in the Az-CH-LA-injected group.

Example 4

Figure 4:
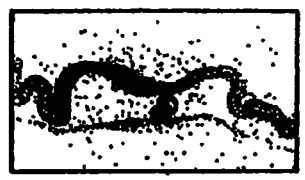
FIG. 4 are microscopic photographs showing cross-sectional views of tissue surrounding the mucous membrane 30 minutes after injection of (a) saline solution and (b) aqueous solution of hyaluronate, and 24 hours after injection, and photo-irradiation of (c) aqueous solution of chitosan derivative containing carbohydrate chains.
Figure 4:
Figure 4:
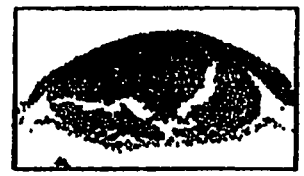
Figure 5:
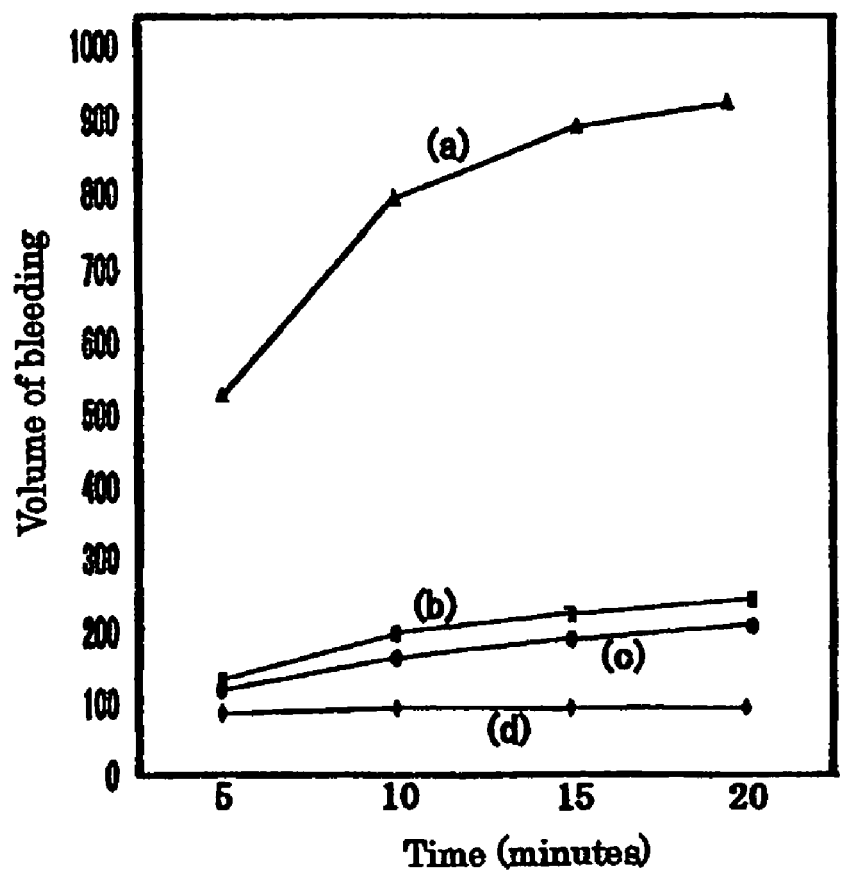
FIG. 5 is a graph showing the time-dependent change in the amount of bleeding after injection of (a) saline, (b) aqueous solution of hyaluronate, (c) aqueous solution of chitosan derivative containing carbohydrate chains (not irradiated) and (d) aqueous solution of chitosan derivative containing carbohydrate chains (photo-irradiated), followed by incision of the mucous membrane.

The same measurements as Examples 2 and 3 were carried out using a liquid composition containing sodium hyaluronate. These results are compared with the results of Examples 2 and 3 in FIGS. 4 and 5. As shown in FIG. 4, in the case where hyaluronate aqueous solution was used, the bulge of the mucous membrane decreased, whereas when the liquid composition of the current invention was used, a clear elevated shape was retained after 24 hours. Furthermore, an extremely excellent anti-bleeding effect was obtained by the liquid composition of the current invention.

Example 5

Change of Viscosity Due to Sterilization with Autoclave

Aqueous solutions of commercially available Az-CH-LA (molecular weight is about 10,000 measured by GPC) were prepared (two types of concentration: 0.5% by weight and 1.0% by weight). These solutions were added to 15 ml conical tubes and sterilized in an autoclave under the following conditions.

(1) at 121° C. for 20 minutes.
(2) at 118° C. for 30 minutes.

Solutions were compared after sterilization. There was no precipitation and a slight coloring (maize) was observed in all solutions.

Viscosity of the each solution was measured before and after sterilization using a rotation viscometer, and the results are shown in the following Table 2.

TABLE 2

| Sterilization Conditions | Viscosity (mPa · s) | |
| --- | --- | --- |
| | Az-CH-La concentration: 0.5% by weight | Az-CH-La concentration: 1.0% by weight |
| No sterilization | 32.8 | 264.0 |
| 121° C. × 20 min. | 12.6 | 46.0 |
| 118° C. × 30 min. | 14.0 | 51.0 |

It is clear from the above results that the viscosities of the aqueous solutions markedly decreased by autoclave sterilization, which made the solution more suitable for topical injection.

In addition, the amount of azide groups in each sample before and after sterilization was measured by UV spectrum and FT-IR. As a result, no decomposition of a photo-reactive (azide) group was observed after sterilization, and the post-sterilization sample included the same amount of azide groups as pre-sterilization sample.

Furthermore, when the samples were cored by light-irradiation, all of the samples could be suitably gelled.

INDUSTRIAL APPLICABILITY

The chitosan derivative containing carbohydrate chains could be used as the liquid composition to make the mucous membrane bulge, as well as the hydrogel formed therefrom by photo-crosslinking show no cytotoxicity in cell-culture tests on human skin fibroblasts, human endothelial cells, and human smooth muscle cells. In addition, toxicity tests for organisms, including mutagenicity and cytotoxicity, demonstrated the safety of the chitosan derivative and its hydrogel. Accordingly, the composition of the present invention is suitable as a liquid (a topically injectable liquid) to make the mucous membrane bulge during endoscopic surgery, such as EMR or ECD.

Furthermore, the composition of the present invention can be provided as a ready-to-use product via sterilization with autoclave.

In addition, the liquid composition of the present invention may of course be used in other general surgical procedures other than in the endoscopic surgery, such as resection of cancer on surface tissue or hemostatic treatment.

The invention claimed is:

1. A method of conducting endoscopic surgery comprising:
targeting mucous membrane of a patient that is in need of bulging during endoscopic surgery;
administering under said targeted mucous membrane a composition comprising a solution in a physiologically acceptable liquid of a chitosan derivative containing carbohydrate chains; and
bulging said targeted mucous membrane as a result of administration of said composition.

2. A method according to claim 1 wherein said composition comprises 0.5 to 8.0% by weight of said chitosan derivative.

3. A method according to claim 2, wherein said composition has a low viscosity of 300 cps (mPa·s) or less.

4. A method according to claim 1 wherein said chitosan derivative is a polymer comprising repeating glucosamin units represented by the following formula (I):

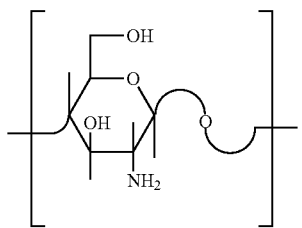

(I)

wherein a carbohydrate chain having a reducing terminal is bonded to the 2-position amino group of one of said glucosamin units.

5. A method according to claim 4 wherein a photoreactive group is bonded to the 2-position amino group of another of said glucosamin units.

6. A method according to claim 5 wherein said photoreactive group is selected from the group consisting of: a carbonylazide group, a sulfonylazide group, an aromatic azide group, a formyl styryl group, and combinations thereof.

7. A method according to claim 5 comprising irradiating said composition with light during surgery.

8. A method according to claim 5, wherein said composition has a low viscosity of 300 cps (mpa·s) or less.

9. A method according to claim 4 wherein said chitosan derivative further contains an amphipathic group.

10. A method according to claim 4, wherein said composition has a low viscosity of 300 cps (mPa·s) or less.

11. A method according to claim 1 wherein said composition is administered by injection.

12. A method according to claim 1, wherein said composition has a low viscosity of 300 cps (mPa·s) or less.

* * * * *